United States Patent [19]
Bornstein et al.

[11] Patent Number: 5,681,822
[45] Date of Patent: Oct. 28, 1997

[54] SOLUBLE 2-CHLORO-2'-DEOXYADENOSINE FORMULATIONS

[75] Inventors: Michael Bornstein, Westfield; Rosemary Rozman; Kevin Francis Long, both of Flemington; George Kaon Wong, Somerville, all of N.J.

[73] Assignee: Ortho Pharmaceutical Corporation, Raritan, N.J.

[21] Appl. No.: 781,438

[22] Filed: Jan. 10, 1997

Related U.S. Application Data

[63] Continuation of Ser. No. 362,083, Dec. 22, 1994, abandoned.

[51] Int. Cl.$^6$ ................................................ A61K 31/70
[52] U.S. Cl. .................................................... 514/46
[58] Field of Search ....................................... 514/46

[56] References Cited

U.S. PATENT DOCUMENTS

| | | | |
|---|---|---|---|
| 4,719,295 | 1/1988 | Cook et al. | 514/46 |
| 4,908,441 | 3/1990 | Cook et al. | 536/27 |
| 5,208,327 | 5/1993 | Chen | 536/27.7 |
| 5,310,732 | 5/1994 | Carson et al. | 514/46 |

*Primary Examiner*—Phyllis G. Spivack
*Attorney, Agent, or Firm*—John Harbour

[57] ABSTRACT

Shelf stable formulations of 2-CdA in water are disclosed which contain benzyl alcohol and, optionally, propylene glycol.

8 Claims, 3 Drawing Sheets

SOLUBLE 2-CHLORO-2'-DEOXYADENOSINE FORMULATIONS

This is a continuation of application Ser. No. 08/362,083, filed Dec. 22, 1994 abandoned.

This invention relates to pharmaceutically useful and soluble formulations of 2-chloro-2'-deoxyadenosine (2-CdA) in water. More particularly, this invention relates to soluble formulations of 2-CdA in water with certain solubilizers and optionally certain preservatives and buffers which am injectable in humans and have a improved shelf-life.

BACKGROUND OF THE INVENTION

The compound 2-CdA has the following formula:

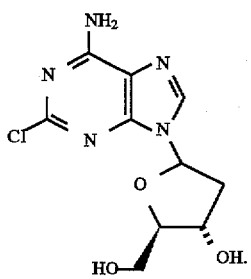

2-CdA is known as an antileukemic agent, i.e., in treating leukemias, such as, hairy cell leukemia and L 1210 leukemia, and as an immunosuppressive agent (D. A. Carson, D. Bruce Wasson, and Ernst Beutler, Proc. Soc. Acad. Sci. U.S.A., Vol. 81, pp 2232–2236, 1984). More recently, 2-CdA has been has been disclosed as effective in the treatment of rheumatoid arthritis and multiple sclerosis, U.S. Pat. No. 5,310,732.

To date, 2-CdA has been administered by intravenous injection of saline solutions presenting two problems for subtaneous or intramuscular injection. First, 2-CdA is slightly soluble in water which requires a large volume of material to be injected subscutaneously or intramuscularly to achieve the required dose. Dilute solutions are acceptable for intravenous injection, but may create pain or inflammatory difficulties for subcutaneous or intramuscular injection. Secondly, 2-CdA has limited stability in simple saline solutions. Longer shelf-life is beneficial for extended storage at refrigerated or room temperature conditions.

U.S. Pat. No. 5,310,732, col. 8, teaches a 0.1 mg/mL isotonic saline solution of 2-CdA. There has been marketed a non-buffered solution containing 1.0 mg/mL of 2-CdA in 9.0 mg/mL Sodium Chloride Injection, USP.

SUMMARY OF THE INVENTION

Figure 1:
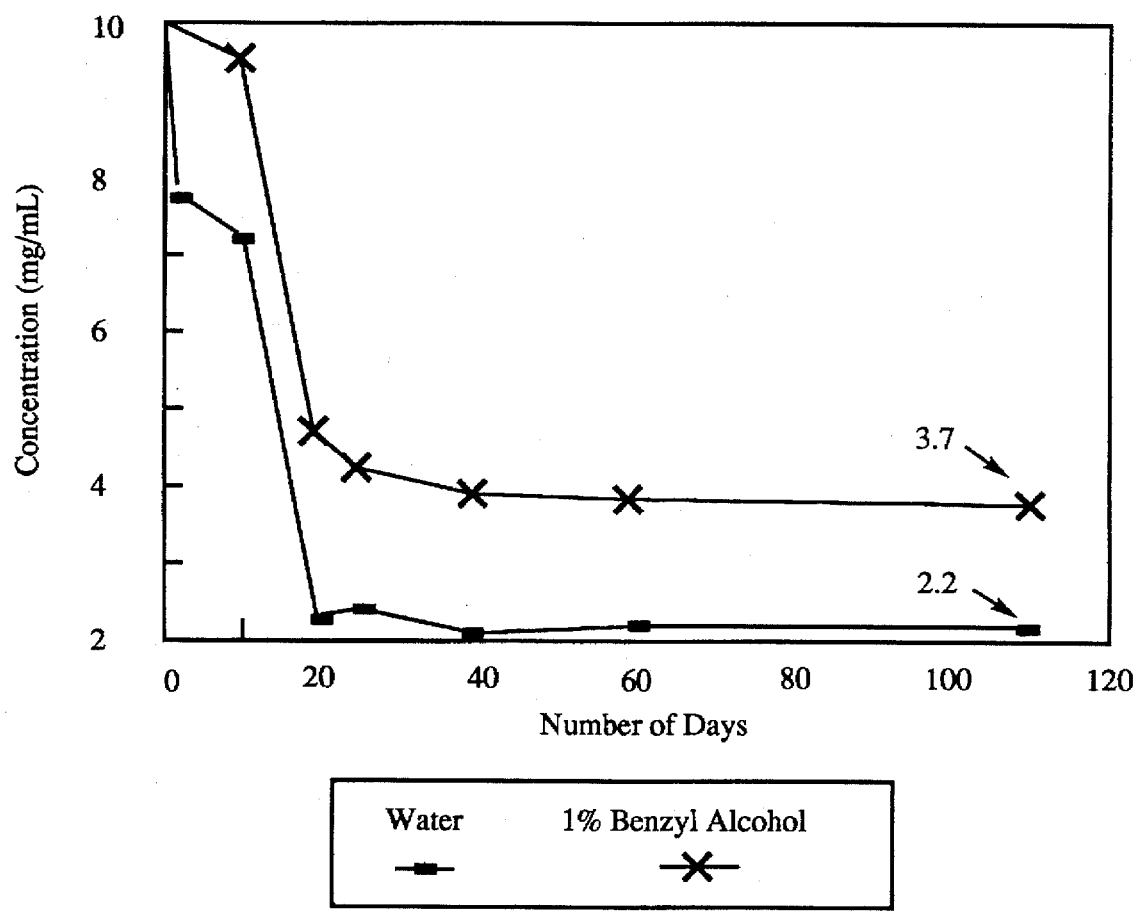
FIG. 1 is the concentration of 2-CdA versus time in water and with 1% benzyl alcohol as a cosolvent.
Figure 2:
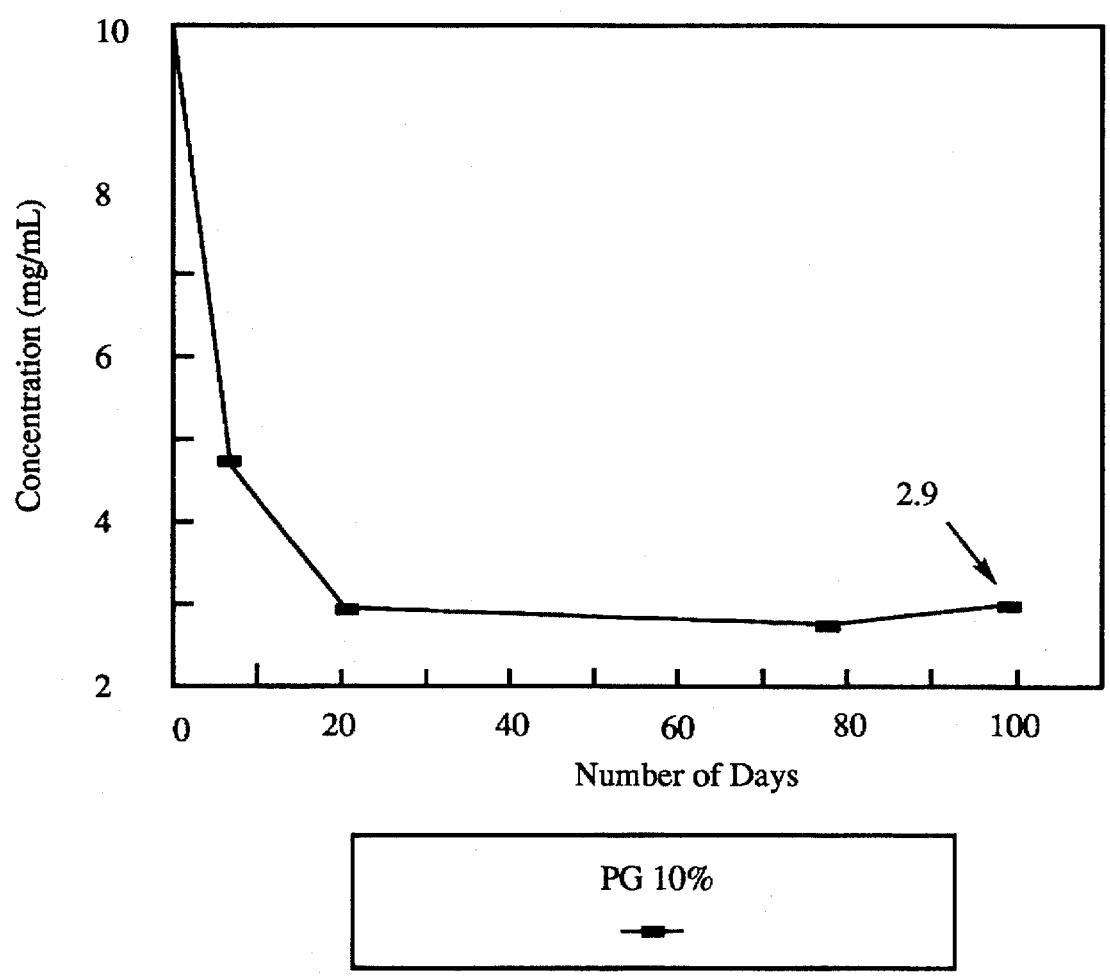
FIG. 2 is the concentration of 2-CdA versus time with 10% propylene glycol as a cosolvent.
Figure 3:
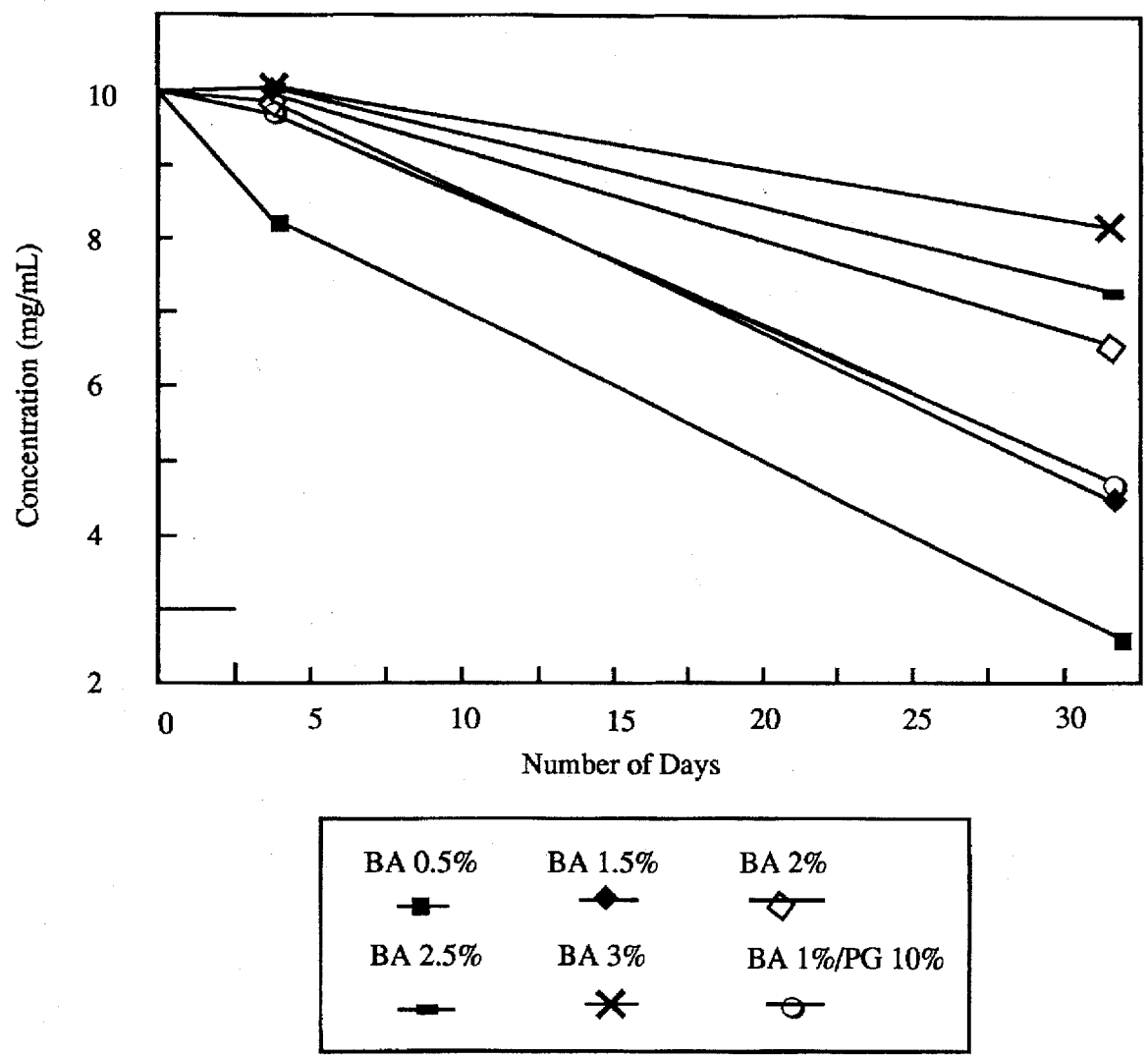
FIG. 3 is the concentration of 2-CdA versus time with various levels of benzyl alcohol and a single combination of benzyl alcohol and propylene gylcol as shown.

There is provided by the present invention a solution of 2-CdA in water comprising:
a) from about 1 to about 8 mg/mL of 2-CdA; and
b) a solubilizing agent selected from the group consisting of from about 5 to about 30 mg/mL of benzyl alcohol and from about 50 to about 400 mg/mL of propylene glycol.

DETAILED DESCRIPTION OF THE INVENTION

Processes for preparing 2-CdA are known. European Patent Application No. 173,059 A2 and Robins et al., J. Am. Chem. Soc., 106, 6379 (1984) disclose the preparation or 2-CdA. The preparation consists of the glycosilation of 2,6-dichloropurine with 1-chloro-2'-deoxy-3',5'-di-O-p-toluoyl-b-D-erythropentofuranose to yield the N-9 glycosylated purine, 2,6-dichloro-9-(2-deoxy-3,5-di-O-p-toluoyl-b-D-erythropentofuranosyl)-purine, which is subsequently reacted with ammonia to yield 2-CdA. An alternative method to manufacture 2-CdA is taught in U.S. Pat. No. 5,208,327 by Robert H. K. Chen.

Preferably, the solution contains from about 2 to about 7 mg/mL of 2-CdA. Most preferably the solution contains from about 3 to about 5 mg/mL of 2-CdA.

Benzyl alcohol is known generally as a preservative in pharmaceutical formulations based on its antibacterial action and as a solubilizing agent for certain pharmaceutical compounds. Preferably, in the solutions of the present invention there is present from about 8 to about 20 mg/mL benzyl alcohol and most preferrably from about 10 to about 15 mg/mL.

Propylene glycol is a known solubilizing agent for a variety of pharmaceuticals. Preferably in the solution of the present invention there is from about 75 to about 200 mg/mL of propylene glycol and most preferrably from about 100 to about 150 mg/mL.

It is preferred that both benzyl alcohol and propylene glycol be present within the prescribed ranges to obtain optimum solubility of 2-CdA in water. Of course, where one of either benzyl alcohol or propylene glycol it is contemplated within the present invention that the other may be present in less that the prescibed minimum amount.

To provide for useful solutions of 2-CdA which may be injected to achieve the desired pharmaceutical effect, it may be necessary or desirable to include further compounds in the formulation.

In the absence of propylene glycol, sodium chloride might be added to render the solution isotonic. Where employed, it might constitute from about 2 to about 6 mg/mL of the solution.

The m-cresol is known generally as a preservative in pharmaceutical formulations based on its antibacterial action. In preferred solutions herein there might be added from about 1.5 to about 2.5 mg/mL of m-cresol and most preferrably about 2 mg/mL.

Suitable buffers are any of those available for pharmaceutical application and which are capable of stabilizing pH for the instant solutions between 5.5 and 8.5. Such buffers include but are not limited to phosphate, citrate, acetate, borate and tris. The preferred buffer for use herein is sodium phosphate buffer. A preferred pH range for the shelf stable solutions herein is between about 6.0 and about 7.0. The ratio of the sodium phophate monobasic, $NaH_2PO_4 \cdot H_2O$, and the sodium phosphate dibasic, $Na_2HPO_4 \cdot 7H_2O$, are adjusted to achieve the pH desired. This buffer is generally useful to achieve a pH in the range of from 4.5 to 8.5. Of course, sufficient buffer should be employed not only to obtain the desired pH but to stabilize the pH at that value. For solutions herein there might be employed a weight ratio from about 2 to 1 to about 1 to 1 of the sodium phosphate monobasic to the sodium phosphate dibasic.

The formulation of Table 1 was prepared and found suitable for use as an injectable and pharmaceutically useful solution. This solution is pH 6.5. All figures shown are in mg/mL. The following abbreviations are employed in Table 1 and elsewhere herein: propylene glycol, USP, (PG), benzyl alcohol, NF, (BA), m-cresol, (MC), sodium phosphate monobasic, monohydrate, USP, (SPMM) and sodium phosphate dibasic, heptahydrate, USP, (SPDH). Water for injection, USP (WFI), was added to 1.0 mL.

TABLE 1

| Formulation | 1 |
|---|---|
| 2-CdA | 5.0 |
| PG | 100.0 |
| BA | 10.0 |
| MC | 2.0 |
| SPMM | 1.816 |
| SPDH | 0.941 |

2-CdA may be administered to a patient in need of the same in a daily dose of 0.05 to about 0.15 mg/Kg. A more desirable daily dose would be from 0.07 to about 0.1 mg/Kg.

The invention is illustrated, but in no way limited, by the following examples.

EXAMPLE

The following solutions were prepared with water for injection to make a total volume of 1.0 mL. All figures are in mg/mL.

TABLE 2

| Formulation | 2-CdA | BA | PG |
|---|---|---|---|
| Control | 10.0 | | |
| 1 | 10.0 | | 100.0 |
| 2 | 10.0 | 5.0 | |
| 3 | 10.0 | 10.0 | |
| 4 | 10.0 | 15.0 | |
| 5 | 10.0 | 20.0 | |
| 6 | 10.0 | 25.0 | |
| 7 | 10.0 | 30.0 | |
| 8 | 10.0 | 10.0 | 100.0 |

The formulations of Table 2 were stored in a darkened container at room temperature and tested periodically for the amount of 2-CdA in solution. The reported figure is 2-CdA in solution in mg/mL.

TABLE 3

| Days | Formulation | | | | | | | | Control |
|---|---|---|---|---|---|---|---|---|---|
| | 1 | 2 | 3 | 4 | 5 | 6 | 7 | 8 | |
| 0 (target) | 10.0 | 10.0 | 10.0 | 10.0 | 10.0 | 10.0 | 10.0 | 10.0 | 10.0 |
| 3 | | | 10.0 | | | | | | 7.65 |
| 4 | | 8.29 | | 9.97 | 9.80 | 10.1 | 9.99 | 9.67 | |
| 6 | 4.71 | | | | | | | | |
| 10 | | | 9.54 | | | | | | 7.30 |
| 17 | | | 4.66 | | | | | | 2.21 |
| 22 | 2.94 | | | | | | | | |
| 24 | | | 4.25 | | | | | | 2.26 |
| 32 | | 2.61 | | 4.42 | 6.25 | 6.85 | 7.92 | 4.71 | |
| 38 | | | 3.64 | | | | | | 2.09 |
| 59 | | 3.63 | | | | | | 2.15 | |
| 74 | 2.66 | | | | | | | | |
| 102 | 2.85 | | | | | | | | |
| 111 | | 3.7 | | | | | | 2.24 | |

It is evident from the data above, that the solubility of 2-CdA in water is greatly increased by the addition of either propylene glycol or benzyl alcohol. Nowhere are co-solvents having such a marked effect on the solubility of 2-CdA taught or suggested in the prior art.

What is claimed is:

1. A solution of 2-CdA in water comprising:

a) from about 2 to about 8 mg/mL 2-CdA; and b) a solubilizing agent which is from about 5 to about 30 mg/mL of benzyl alcohol.

2. The solution of claim 1 comprising from about 2 to about 7 mg/mL of 2-CdA.

3. The solution of claim 1 comprising from about 3 to about 5 mg/mL of 2-CdA.

4. The solution of claim 1 wherein the solubilizing agent is from about 8 to about 20 mg/mL of benzyl alcohol.

5. The solution of claim 1 wherein the solubilizing agent is from about 10 to about 15 mg/mL of benzyl alcohol.

6. The solution of claim 1 wherein the solubilizing agent further comprises from about 50 to about 400 mg/mL of propylene glycol.

7. The solution of claim 1 wherein the solubilizing agent further comprises from about 75 to about 200 mg/mL of propylene glycol.

8. The solution of claim 1 wherein the solubilizing agent further comprises from about 100 to about 150 mg/mL of propylene glycol.

* * * * *